United States Patent [19]
Bailey

[11] Patent Number: 5,156,547
[45] Date of Patent: Oct. 20, 1992

[54] DISPOSABLE PROPHYLAXIS ANGLE AND METHOD OF ASSEMBLING

[75] Inventor: Ronald L. Bailey, Harvester, Mo.

[73] Assignee: Young Dental Manufacturing Company, Earth City, Mo.

[21] Appl. No.: 613,366

[22] Filed: Nov. 15, 1990

[51] Int. Cl.$^5$ .............................................. A61C 3/06
[52] U.S. Cl. .................... 433/125; 433/126; 433/166
[58] Field of Search .................... 433/125, 166, 126

[56] References Cited

U.S. PATENT DOCUMENTS

| | | | |
|---|---|---|---|
| 2,738,528 | 3/1956 | Fridge, Sr. | 433/166 |
| 3,163,934 | 1/1965 | Wiseman | 433/125 |
| 3,389,468 | 6/1968 | Lewis et al. | 433/80 |
| 3,407,502 | 10/1968 | Richmond | 433/134 |
| 3,672,060 | 6/1972 | Eibofner et al. | 433/127 |
| 3,727,313 | 4/1973 | Graham | 433/125 |
| 3,798,777 | 3/1974 | Reiter | 433/125 |
| 4,040,311 | 8/1977 | Page, Jr. et al. | 433/129 |
| 4,053,983 | 10/1977 | Flatland | 433/126 |
| 4,182,041 | 1/1980 | Girard | 433/115 |
| 4,266,933 | 5/1981 | Warden et al. | 433/82 |
| 4,285,671 | 8/1981 | Lustig et al. | 433/126 |
| 4,449,932 | 5/1984 | Lustig | 433/126 |
| 4,544,356 | 10/1985 | Gardella et al. | 433/125 |
| 4,564,354 | 1/1986 | Rosenstatter | 433/133 |
| 4,604,058 | 8/1986 | Fisher et al. | 433/125 |
| 5,020,994 | 6/1991 | Huang | 433/125 |
| 5,028,233 | 7/1991 | Witherby | 433/125 |
| 5,040,978 | 8/1991 | Falcon et al. | 433/125 |
| 5,040,979 | 8/1991 | Kuhn | 433/126 |

Primary Examiner—John J. Wilson
Attorney, Agent, or Firm—Polster, Lieder, Woodruff & Lucchesi

[57] ABSTRACT

A plastic, disposable, easy-to-assemble dental angle is provided. The angle includes a one-piece hollow body having a head at its front end which is angled with respect to the body. Both the head and the body have a bore therethrough. The head has an aperture which is centered with respect to the bore of the body to allow insertion of a drive gear through the head of the angle. A driven gear is inserted in the head from above. A snap cap fits within the head over the driven gear to lock both the drive gear and the driven gear in the angle. A sheath on the cap covers the aperture. A latch on the cap is received in the aperture to lock the cap to the head to hold the angle together. An elongated slot in the body permits the body to be force-fit on a dental handpiece. In one embodiment, the length of the angle is shortened so that the thrust load produced during use is carried by a rolling contact in the handpiece to which the angle is secured, rather than by a sliding, friction-producing, contact between the drive gear's shaft and the surfaces of the angle itself.

13 Claims, 2 Drawing Sheets

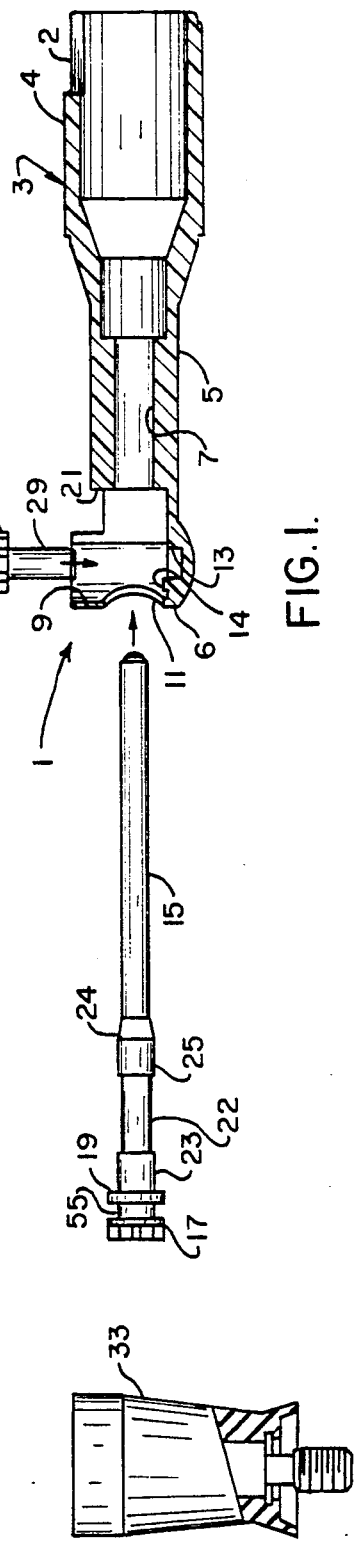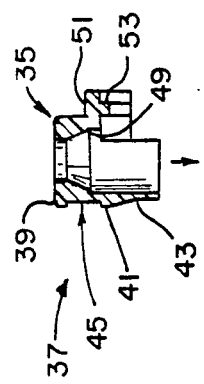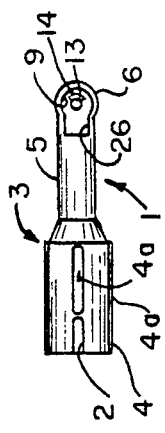

DISPOSABLE PROPHYLAXIS ANGLE AND METHOD OF ASSEMBLING

BACKGROUND OF THE INVENTION

This invention relates to dental or prophylaxis angles, and, in particular, to a disposable dental angle.

Dental angles carry dental bits such as prophy cups and brushes. The angle enables dentists to reach more easily the various surfaces of a patient's teeth and thus facilitates the cleaning of the teeth. These angles generally include a body having a head thereon which has a major axis angled relative to the major axis of the body. The angle is commonly 90°. A drive gear and a driven gear are carried in the body in a meshing relationship. The driven gear carries a desired dental bit, such as a cleaning cup or a brush, which is to be used during the cleaning procedure. The body is slipped over the nose of a handpiece such as a Doriot type handpiece having a collet which receives the shaft of the drive gear. The collet holds the shaft, hence the angle, against axial movement. It also connects the drive gear to a motor, to rotate the drive gear, and thus the dental bit.

The use of disposable dental angles reduces the labor, cost, and risks of sterilization.

A first type of prior art disposable dental angle includes a two-piece body and is formed as a sandwich. The gears are placed in the first half of the body. The second half is then placed on top of the first half and the body is then joined such as by ultrasonic welding. However, when this type of dental angle is fitted over a collet of a Doriot handpiece, the forces exerted by the collet on the body tend to separate the body along its seams. Further, to avoid the possibility of welding the gears to the body when welding the body, the gears must fit loosely in the body. This leads to a loose fit between the gears and thus the gears do not run very smoothly.

A second type of prior art angle includes a one-piece body which receives the drive gear from its rear such as is shown and described in U.S. Pat. No. 3,727,313 to Graham. A latch snaps in place behind a shoulder on the drive gear to lock the drive gear in place. However, the latch has a tendency to unhitch, allowing the drive gear to move axially within the body and to come out of contact with the driven gear. This frees the driven gear, allowing it to fall out of the head. This will cause obvious problems, especially if the latch comes undone during a cleaning procedure. The driven gear is positioned between the drive gear, and the head is thus held in place by the drive gear. Because the driven gear is placed below the drive gear, rather than above it, the dental bit rotates in an opposite direction from most other dental bits. This creates problems for hygienists who are accustomed to these other angles. During operation, the dental bit tends to "walk" due to the rotational contact with the tooth. A hygienist who has learned to compensate for "walk" in one direction, will have to become accustomed to compensating for "walk" in the opposite direction. There is, therefore, a "learning period" associated with this type of angle.

With either type of angle, the drive gear, particularly its shaft at the point where it narrows to its constant diameter, tends to overheat and fail.

SUMMARY OF THE INVENTION

One object of the invention is to provide a dental angle which is rugged and will not come apart.

Another object is to provide such a dental angle which runs smoothly and without overheating or failing, even for extended periods at high rotational speeds.

Another object is to provide such a dental angle which is easy to assemble.

Another object is to provide such a dental angle which is inexpensive to produce.

Another object is to provide such an angle which provides rotation in the conventional direction.

Another object is to provide a dental angle in which the thrust load produced during use of the angle is carried by a rolling contact, rather than a sliding contact.

These and other objects will become apparent to those skilled in the art in light of the following disclosure and accompanying drawings.

In accordance with the present invention, generally stated, a disposable dental angle is provided comprising a one-piece body having an axial bore extending completely through it and a head integral with the body at one end thereof. The body bore extends through an exterior wall of the head, forming an aperture at the front of the head and aligned with the body bore. The head has an axial bore therein, at an angle to the body bore, terminating in a pilot bearing at the bottom of the head bore. A drive gear on a shaft is inserted into the body bore through the aperture, shaft first, and a driven gear is inserted through the head bore to be in meshing contact with the drive gear. The driven gear carries a dental bit, such as a prophy cup or brush.

The angle also includes a cap having locking means for locking the drive gear and the driven gear in place. The locking means comprises a latch on the cap which is received in the aperture. A sheath on the cap extending below the latch covers the aperture. The cap further includes a retaining shoulder which covers the driven gear to prevent vertical (axial) movement of the driven gear.

The body further includes a second aperture, extending rearwardly from the head, which exposes the drive gear. A circumferential flange on the drive gear shaft behind the drive gear forms a groove with the drive gear. The cap preferably includes a rear lip which covers the second aperture and which includes a downwardly extending finger which is received in the groove to prevent axial movement of the drive gear. The cap acts as a retainer, a shield, and a radial bearing.

The rear end of the body aperture is defined by a cylindrical sleeve part which is proportioned to form a friction fit with the nose of the Doriot handpiece. An axial slot in the skirt is longer than required to fit over a pin on the nose of the handpiece, to permit the skirt to expand sufficiently to form a tight, friction fit with the nose. The body of the angle is thus secured axially to the handpiece independent of the chuck holding the shaft of the drive gear. It has been found that one of the causes of heating and failure of conventional disposable angles is that the operator tends to push the body of the angle forward in use, thereby causing an axial load on the drive gear. The size-on-size fit of the present angle on the handpiece prevents movement of the angle's body with respect to the shaft, both axially and angularly, and thus reduces friction and heat in use.

In another embodiment, a dental angle comprising a body and a head which carries gears in a meshing relationship is provided. The body is mounted on a handpiece having drive means which receives a shaft of one of the gears to drive the gears. The distance between the head and the handpiece is sufficiently short that the load created when the dental bit is urged against a surface is transmitted to and substantially carried by the handpiece. The drive means preferably includes a collet or chuck which rotates on anti-friction ball bearings in the handpiece. The collet receives the gear shaft. The load is transferred along the shaft to the collet. The ball bearings provide a rolling contact between the collet and the handpiece so that the load is carried by the rolling contact.

The optional placing of silicone grease on the gears allows the gears to be operated at speeds in excess of 3,000 rpm. This allows for the use of drill bits on the angle.

BRIEF DESCRIPTION OF THE FIGURES

FIG. 1 is an exploded view, partially in cross section, of an angle of the present invention.

FIG. 2 is a cross-sectional view of the angle of FIG. 1, assembled.

FIG. 3 is a bottom plan view of a body of a dental angle of the present invention.

FIG. 4 is a perspective view of a snap cap used to lock the components of the angle in the body.

DESCRIPTION OF THE PREFERRED EMBODIMENT

Figure 5:
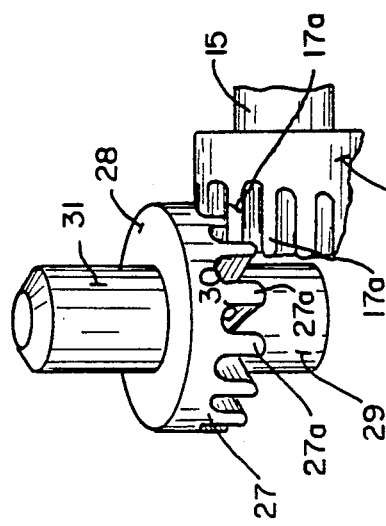
FIG. 5 is perspective view of a drive gear and a driven gear in meshing contact.

Referring to FIGS. 1-3, reference numeral 1 generally indicates a dental angle of the present invention. Angle 1 includes a one-piece body 3, a drive gear 17, a driven gear 27, and a cap 35. All the pieces are preferably molded of plastic so that angle 1 will be inexpensive to produce and thus disposable. This eliminates the need to sterilize angles and their associated bits between uses and thus eliminates any problem of cross-contamination between patients. It has been found that when dissimilar plastics are used for the body, cap, and gears, the angle operates more smoothly. Thus, it is preferred that the body and cap be made from a hard plastic such as a polycarbonate resin available from General Electric Co. under the trademark LEXAN, and that the gears be made from a more flexible plastic, such as a self-lubricating acetal copolymer available from Celanese Corp. under the trademark CELCON.

Body 3 includes a sleeve 4, a neck 5, and a head 6 formed integrally therewith. Sleeve portion 4 is formed as a cylinder, having thin reinforcing ribs 4a. The wall thickness of the sleeve 4 is about 0.04". A slot 2 at the rear, open, end of the sleeve 4 is about 0.250" long and about 0.1" wide. The slot 2 is about twice as long as necessary to accommodate a standard positioning pin or finger on a standard Doriot type handpiece. The length of the slot 2 and the thinness of the plastic sleeve wall in which it is formed permit the sleeve to expand slightly when it is forced onto a Doriot handpiece. The forward end of the sleeve portion 4 tapers to the neck portion 5, which is a smaller diameter cylinder coaxial with the sleeve 4. The head portion 6 is formed as a cylinder at right angles to the neck 5, with the axis of the head 6 intersecting the axis of the neck 5.

Body 3 and head 6 have axial bores 7 and 9, respectively.

Body bore 7 is formed with several diameters. In the sleeve portion 4, bore 7a is formed with the same diameter as the nose of a standard Doriot handpiece. It tapers as at 7b in the transition between sleeve 4 and neck 5, to a smaller diameter portion 7c in the neck 5, then steps to a yet smaller diameter portion 7d through the forward part of the neck 5. The portion 7d acts as a journal for the drive gear shaft, as described hereinafter. Forward of the small diameter portion 7d, the bore 7 steps to a larger diameter portion 7e, extending through the head portion 6 and forming an aperture 11 in the forward end of the head 6.

Head bore 9 is formed at a 90° angle with respect to body bore 7. At the lower end of the head 6 head bore 9 forms a blind hole 13 centered with respect to the head bore 9. A crescent-shaped rib 14 on the forward side of the blind hole 13 is spaced a short distance from the forward wall of the head.

Figure 6:
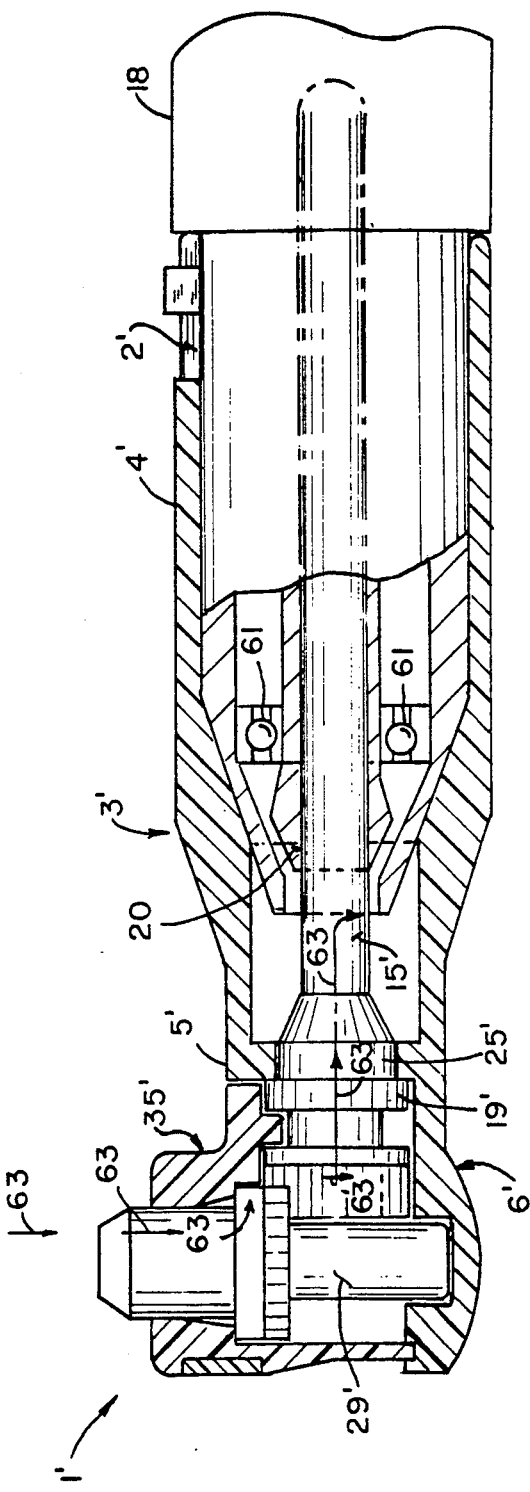
FIG. 6 is a cross-sectional view of a second embodiment of the present invention.

Drive gear 17, which is fixed to one end of a drive gear shaft 15, is received in body bore 7 through aperture 11. Shaft 15 extends beyond the end of body 3 when inserted therein to facilitate the capture of drive shaft 15 by chuck jaws 20 in a handpiece 18, such as a collet 20 in a Doriot handpiece (FIG 6). Collet 20 holds shaft 15 so that it may be driven by an air motor in handpiece 18, as is well known in the art.

A flange 19 on shaft 15, spaced behind gear 17, butts up against a shoulder 21 in body 3 to properly position shaft 15 and hence gear 17 in body 3. About 0.125" behind the flange 19, the shaft 15 is slightly relieved for about 0.250", as indicated at 22, to form a forward bearing surface 23 and a rear bearing surface 25. The bearing surfaces 23 and 25 form a smoothly rotatable fit with the forward and rearward portions of the neck portion 7d of the body bore 7. A conical section 24 behind the rear bearing surface 25 provides a transition to a smaller-diameter rearward stem section of the shaft 15. The conical section 24 reinforces the stem 15 at its weakest point and helps to transfer heat from the bearing section 25.

When properly positioned, gear 17 is slightly behind blind hole 13. A rectangular opening 26 on body 3 at the junction of the head 6 and sleeve 5 exposes gear 17 and flange 19.

Driven gear 27, which is fixed to a shaft 29, is received in head bore 9. Blind hole 13 receives shaft 29 to center gear 27 in head bore 9. When inserted in head bore 9, driven gear 27 meshes with drive gear 17 to be driven thereby. Drive gear 17 does not contact shaft 29. A boss 31 on top of driven gear 27 receives a dental bit, such as a prophy cup 33.

As can be seen in FIG. 5, the teeth 27a of gear 27 preferably do not extend all the way through the gear. Rather, the gear has a planar cap 28 above teeth 27a. Further, the spaces 30 between the tops of teeth 27a are contoured. Because gear teeth 17a of gear 17 radiate outwardly from the root of gear 17, the teeth 27a do not extend into the spaces between teeth 17a to the point where the width of the space between teeth 17a is equal to the width of tooth 27a. Thus, the contact between gears 17 and 27 occurs in the space 30 between teeth 27a, rather than in the root of drive gear 17. This creates a rolling contact between the gears, allowing the gears to run more smoothly.

A snap cap 35 (FIG. 4) is received in head bore 9 to lock gears 17 and 27 and their associated shafts in place in body 3. At its forward end 37, cap 35 includes a lip 39, a latch 41 and a sheath 43. The lip 39 and sheath 43 extend about 280° around the front of the cap 35. Sheath 43 has an outer diameter equal to the diameter of the head bore 9 and fits snugly into the head bore 9. Lip 39 and latch 41 define a section 45 of sheath 43 which is sufficiently wide to fit around a portion 47 of head 6 between aperture 11 and the top of head 6. Latch 41 slopes upwardly and outwardly from sheath 43. Thus, when cap 35 is inserted into head 6, head portion 47 is urged outward until the cap is in place. Portion 47 then snaps back above latch 41 securely locking snap cap 35 into place such that it is difficult to remove. Lip 39 extends over the top of head portion 47 and thus aids in preventing vertical movement of cap 35 to help lock the cap in place. Sheath 43 covers aperture 11 to prevent cleaning abrasive or other substances from entering head 6 during use. The free lower end of the sheath 43 fits into the space between the head bore 9 and the crescent rib 14 adjacent the blind hole 13.

To limit vertical movement of driven gear 27, cap 35 includes an annular shoulder 49 which accommodates gear 27. Planar surface 28 of gear 27 contacts shoulder 49, presenting a smooth contact between the two pieces rather than the non-continuous, possibly irregular surface which would be presented if teeth 27a extended the height of gear 27. Boss 31 extends above cap 35 to receive dental bit 33. The inner surface 50 of cap 35, which surrounds boss 31, tapers away from boss 31 to create a space 52 between boss 31 and surface 50. This space reduces the friction creating area between boss 31 and surface 50 allowing for smoother operation of the angle. It also creates an area through which cleaning abrasive may fall, thereby reducing galling caused by the action of the abrasive which enters head 6.

At its rear, cap 35 includes a lip 51 which fills body aperture 26. Lip 51 includes a downwardly extending finger 53 which fits in a groove 55 formed by drive gear 17 and flange 19 to prevent axial movement of gear 17 and shaft 15. Thus, gear 17 will not impinge on driven gear shaft 29, as previously noted.

To assemble angle 1, drive gear 17 and its associated shaft 15 are inserted, shaft first, into body 3 through aperture 11 until the flange 19 abuts the shoulder 21. Driven gear 27 is then inserted into head 6 from above the head until it meshes with gear 17. Cap 35 is then placed into head 6, closing up the assembly and locking the gears in place. A desired dental bit may then be inserted into boss 31 and the angle may be connected to the handpiece. As previously noted, the sleeve 4 forms a size-on-size fit with the nose of the handpiece, the extended slot 2 permitting the free end of the sleeve to expand sufficiently for easy mounting. The body 3 of the angle 1 therefore does not move axially or angularly during use and is held onto the handpiece independent of the capture of the stem 1 by the collet of the handpiece.

A second embodiment of the angle is shown in FIG. 6 and is designated 1'. Angle 1' is substantially similar to angle 1. However, body 3' has a substantially shorter neck 5' than the neck 5 of angle 1. Further, drive gear shaft 15' has only one bearing surface 25', located behind flange 19' at the entrance to sleeve 5'. Angle 1' has the advantage of transferring the load produced during use to collet 20 rather than to a friction creating surface as in angle 1. Collet 20 rotates on anti-friction ball bearings 61 in handpiece 18. The load is thus carried by a rolling contact rather than a sliding, friction-producing contact, allowing for an easier rotation of gear 17.

In angle 1', the load follows the path shown by arrows 63. The load initially bears down on driven gear 27 and is transferred to drive gear 17. The load then is transferred axially along drive gear shaft 15' to collet 20 which rotates on ball bearings 61 in handpiece 18. There are gaps between driven gear shaft 29' and head blind hole 13', between flange 19' and cap 35' and head 6', and between drive gear shaft sleeve 25' and body sleeve 5'. Therefore, there is no sliding contact between the gears and the body in angle 1' and all the load is carried by collet 20. In contrast, in angle 1' the load is transferred to bearings 23 and 25 and the bore 7d in neck 5 through driven gear 27, drive gear 17 and shaft 15. Therefore, shortening neck 5 to the length of neck 5' enhances the operation of dental bit 33 by substantially reducing the friction bearing surfaces along which the load forces are transmitted. Neck 5' is preferably shortened by a length equal to the distance between the front of shaft bearing 23 and the front of shaft bearing 25 (i.e., 0.375"), so that sleeve 25' is adjacent shaft flange 19'.

When either of the angles 1 or 1' is assembled, it has been found that if a little bit of silicone grease is placed on gears 17 and 27 and in relieved area 22, the angle can operate at speeds upward of 7,000 rpm for extended periods of time. At speeds upward of 20,000 rpm, the gears operate for only a few minutes before melting. The ability of the gears to operate at such high speeds allows for drill bits to be used with the disposable angle. This allows the same sterile advantages obtained by disposable angle and prophylaxis cup assembles to be obtained by drill bits.

Numerous variations, within the scope of the appended claims, will be apparent to those skilled in the art in light of the foregoing description and accompanying drawings.

I claim:

1. A plastic, disposable dental angle comprising:
   a one-piece body having a sleeve part with an open rear end, a neck part, and a head part including a back adjacent said sleeve and a front, a first axial bore extending through the sleeve and neck part, a second axial bore in the head part, said first and second bores communicating with each other at an intersection and being at an angle with respect to each other, and receiving means at the front of said head part;
   a one-piece drive gear including a gear part and a shaft part, said shaft part extending rotatably through said first bore, said gear part extending into said second bore;
   said receiving means at the front of said head part being in axial alignment with said first bore and proportioned to permit said drive gear to be inserted through said receiving means shaft first;
   a driven gear rotatably mounted in said head bore and operatively connected to said drive gear, said driven gear including means for retaining a dental bit; and
   a cap mounted to said head part, said cap including means for locking said drive gear and said driven gear in said angle.

2. The dental angle of claim 1, wherein said receiving means comprises an aperture in said head, said aperture being centered with respect to said body bore.

3. The dental angle of claim 2, wherein said locking means further comprises a latch on said cap said latch being received in said aperture.

4. The angle of claim 3, wherein said cap further includes a sheath which covers said head aperture.

5. The dental angle of claim 1 wherein the diameter of the first bore in said neck part is too small to admit the gear part of said drive gear.

6. The dental angle of claim 1 wherein said locking means comprises a shoulder in said cap, said shoulder cooperating with said driven gear to limit vertical movement of said driven gear, wherein said body includes an aperture between said neck part and said head part, said aperture exposing said drive gear, wherein said drive gear shaft includes a flange spaced behind said drive gear forming a groove with said drive gear, and wherein said locking means further comprises a rear lip on said cap which covers said aperture, said lip having a finger which is received in said groove, thereby limiting axial movement of said drive gear in said body.

7. The angle of claim 1 wherein the sleeve part includes a groove at its open end, the groove being at least about 0.2" long, the wall thickness of the sleeve part being sufficiently thin to permit opening of said groove when said sleeve part is inserted onto a handpiece.

8. The angle of claim 1, wherein said body is of a sufficiently short length such that the load created during use is substantially borne by said handpiece.

9. The angle of claim 8, wherein said load is carried by a rolling bearing in said handpiece.

10. A disposable dental angle comprising:
a one-piece body comprising a sleeve having an axial bore therethrough, a head integral with said body, said head including a back side adjacent said sleeve and a front side spaced from said sleeve, said head having an axial bore therein, said head bore and said sleeve bore being at an angle with respect to each other; and aperture means in said front side of said head for receiving a one-piece drive gear including a gear on a shaft, shaft first, into said sleeve aperture;
a driven gear in said head bore operatively connected to said drive gear; and
means for limiting axial movement of said driven gear.

11. The dental angle of claim 10 wherein said axial movement limiting means comprises a cap which is received in said head, said cap including an internal shoulder which cooperates with said driven gear to limit axial movement of said driven gear.

12. A method of assembling a dental angle including a one piece hollow body having a hollow head thereon, said head having an aperture at the front of said body centered with respect to said body, said method comprising:
inserting a drive gear which is integral with a drive gear shaft, shaft first, into said body through said aperture in said head;
inserting a driven gear into said head until said driven gear is operatively connected to said drive gear; and
locking said drive gear and said driven gear in said angle.

13. The method of claim 12, wherein said locking step comprises snapping a cap in place in said head, said cap including a latch which is received in said aperture to hold said cap in place.

* * * * *